(12) United States Patent
Appel et al.

(10) Patent No.: US 8,017,801 B2
(45) Date of Patent: Sep. 13, 2011

(54) METHOD FOR PRODUCING ACYL PEROXIDES

(75) Inventors: Hans Appel, Penzberg (DE); Wilfried Meichelböck, Krailling (DE); Josef Helmut Weinmaier, Mühldorf (DE); Helmut Zellner, Hörbach (DE)

(73) Assignee: United Initiators GmbH & Co. KG, Pullach (DE)

( * ) Notice: Subject to any disclaimer, the term of this patent is extended or adjusted under 35 U.S.C. 154(b) by 76 days.

(21) Appl. No.: 12/309,161

(22) PCT Filed: Jun. 18, 2007

(86) PCT No.: PCT/EP2007/056013
§ 371 (c)(1),
(2), (4) Date: Oct. 7, 2009

(87) PCT Pub. No.: WO2008/006668
PCT Pub. Date: Jan. 17, 2008

(65) Prior Publication Data
US 2010/0022794 A1    Jan. 28, 2010

(30) Foreign Application Priority Data
Jul. 12, 2006  (DE) .......................... 10 2006 032 166

(51) Int. Cl.
*C07C 381/00* (2006.01)
(52) U.S. Cl. ....................................... 560/302
(58) Field of Classification Search .......... None
See application file for complete search history.

(56) References Cited

U.S. PATENT DOCUMENTS

| 2,567,615 A | * | 9/1951 | Milas ........................... 560/302 |
| 3,849,468 A | * | 11/1974 | Busseret ....................... 558/269 |
| 5,012,010 A | | 4/1991 | Suyama et al. |
| 5,117,047 A | | 5/1992 | Suyama et al. |
| 6,224,845 B1 | | 5/2001 | Pennetreau et al. |

FOREIGN PATENT DOCUMENTS

| DE | 19 50 536 A1 | 4/1970 |
| EP | 0478 214 A2 | 4/1992 |

OTHER PUBLICATIONS

Kirk-Othmer, Kirk-Othmer Encyclopedia of Chemical Technology, 1993, vol. 10, John Wiley & Sons, New York, p. 153.*
Blomquist, et al. "the Kinetics of the Thermal Decomposition of Peresters. III. The Effect of *p*-Substituents on the Unimolecular Decomposition of *t*-Butyl Perbenzoates", *J. Am. Chem. Soc.*, vol. 73, (1951), pp. 5546-5550; XP-002453452.
Milas, et al. "Studies in Organic Peroxides. IX. *t*-Butyl Peresters", *J. Am. Chem. Soc.*, vol. 68 (1948), pp. 642-643; XP-002453451.

* cited by examiner

*Primary Examiner* — Paul A Zucker
(74) *Attorney, Agent, or Firm* — Fulbright & Jaworski L.L.P.

(57) ABSTRACT

The invention relates to a method for producing acyl peroxides. According to the method, an acyl compound is reacted with an organic hydroperoxide and a base, to generate a two-phase mixture. The pH of the two-phase mixture is adjusted to 6 to 13. The obtained organic phase is extracted with an aqueous solution of a base and the aqueous extract is recirculated to the reaction step. The method according to the invention allows the recirculation of unreacted hydroperoxide to the reaction step.

13 Claims, 1 Drawing Sheet

US 8,017,801 B2

METHOD FOR PRODUCING ACYL PEROXIDES

RELATED APPLICATIONS

Figure 1:
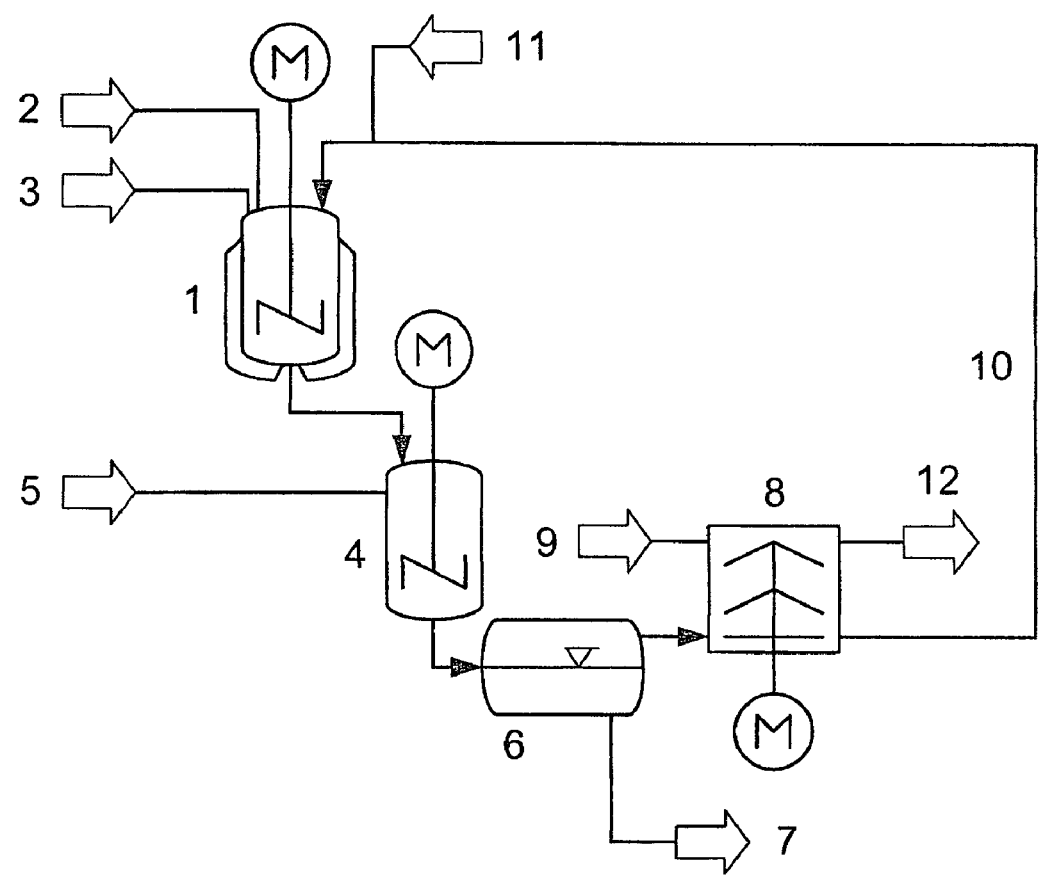

This application is a §371 of PCT/EP2007/056013 filed Jun. 18, 2007, which claims priority from German Patent Application No: 10 2006 032 166.9 filed Jul. 12, 2006.

The invention is directed to a process for preparing acyl peroxides from organic hydroperoxides, in which unconverted hydroperoxide is recovered and recycled into the reaction.

Acyl peroxides are typically prepared by reacting an acyl compound from the group of the acid chlorides, carboxylic anhydrides and chloroformates with an organic hydroperoxide. The reaction is effected with addition of an aqueous solution of a base in order to bind the acid released in the reaction of the acyl compound with the hydroperoxide. The reaction is effected in a biphasic reaction mixture and proceeds exothermically.

For the later use, the acyl peroxides have to be substantially free of the acyl compound used. The organic hydroperoxide is therefore typically used in a stoichiometric excess relative to the acyl compound in order to achieve a maximum conversion of acyl compound. Unconverted organic hydroperoxide then remains in the reaction.

U.S. Pat. No. 2,567,615 discloses the preparation of peroxy esters by reacting an acid chloride or carboxylic anhydride with a tertiary alkyl hydroperoxide in the presence of an alkali metal hydroxide. As is evident from Examples 8, 9 and 10, in which the alkyl hydroperoxide is used in excess, washing of the organic phase obtained in the reaction with 10% by weight of sodium carbonate and with water affords a product which, besides the peroxy ester, comprises as yet unconverted alkyl hydroperoxide.

U.S. Pat. No. 3,138,627 discloses the analogous preparation of tert-butyl peroxy esters of lower aliphatic carboxylic acids using a solvent. The document gives the person skilled in the art the teaching of removing the peroxy esters very rapidly from the alkaline mixture in order to prevent hydrolysis by the basic solution.

U.S. Pat. No. 4,075,236 discloses a continuous process for preparing peroxy esters in which an acid chloride is reacted with a hydroperoxide and an alkali metal hydroxide, wherein a biphasic reaction mixture is obtained. In the reaction, the hydroperoxide is used in an excess of 0 to 50%. The pH of the aqueous phase is in the range of 10 to 14. After the reaction, the aqueous phase is removed and the organic phase is washed in a plurality of mixer-settler stages. The aqueous phases are all discarded. Recovery of unconverted hydroperoxide is not disclosed.

U.S. Pat. No. 3,849,468 discloses a continuous process for preparing acyl peroxides, in which, in a biphasic reaction mixture, an acid chloride is reacted with hydrogen peroxide or a tertiary hydroperoxide in the presence of a solvent, and sodium hydroxide is added in order to establish a pH in the range of 3 to 10. The tertiary hydroperoxide is used in a molar excess of 10 to 20%. In the process, the reaction is effected in a loop reactor from which, in each circulation of the reaction mixture, the organic phase and some of the aqueous phase are removed and fed to a wash column in which the organic phase is washed in countercurrent with water. The aqueous phase obtained in the wash column is discarded. Recovery of unconverted hydroperoxide is not disclosed.

There is therefore a need for a process for preparing acyl peroxides from organic hydroperoxides, in which unconverted hydroperoxide can be recovered and recycled into the reaction and with which an acyl peroxide is obtained which has a low content of unconverted hydroperoxide.

The invention provides a process for preparing acyl peroxides by reacting an acyl compound from the group of the acid chlorides, carboxylic anhydrides and chloroformates with an organic hydroperoxide, comprising the steps of
a) reacting the acyl compound, the organic hydroperoxide and an aqueous solution of a base to obtain a biphasic reaction mixture,
b) adjusting the pH of the aqueous phase of the reaction mixture obtained in step a) to a value in the range of 6 to 13, preferably 11 to 12.5,
c) separating the biphasic mixture obtained in step b) into an aqueous phase and an organic phase,
d) extracting the organic phase obtained in step c) with an aqueous solution of a base and
e) recycling the aqueous extract obtained in step d) into step a).

The process according to the invention comprises, in step a), the reaction of an acyl compound from the group of the acid chlorides, carboxylic anhydrides and chloroformates with an organic hydroperoxide with addition of an aqueous solution of a base. The bases used may be water-soluble metal hydroxides, water-soluble quaternary ammonium hydroxides or water-soluble tertiary amines. The base used is preferably an alkali metal hydroxide or an alkaline earth metal hydroxide, more preferably sodium hydroxide or potassium hydroxide. The reaction affords a biphasic reaction mixture which comprises an organic phase and an aqueous phase. The organic phase comprises the acyl peroxide formed in the reaction. The aqueous phase comprises the chloride salt or carboxylate salt formed in the reaction of the acyl compound with the hydroperoxide. In addition, carboxylate salt which has been formed by reaction of the acyl compound with the base may also be present in the aqueous phase. Unconverted organic hydroperoxide may be present both in the organic phase and in deprotonated form as the hydroperoxide salt in the aqueous phase, the distribution of the hydroperoxide between organic phase and aqueous phase depending on the pH of the aqueous phase and the partition coefficient of the organic hydroperoxide between the aqueous phase and the organic phase.

In the subsequent step b), in the biphasic reaction mixture which is obtained in step a), the pH of the aqueous phase is adjusted to a value in the range of 6 to 13, preferably 11 to 12.5. The pH is preferably selected at such a low level that more than 50%, more preferably more than 80%, of the unconverted organic hydroperoxide is present in the organic phase and only a small portion is present in deprotonated form as the hydroperoxide salt in the aqueous phase. The selection of a sufficiently low pH allows the proportion of organic hydroperoxide which is removed with the aqueous phase in step c) to be kept low and thus ensures that the majority of the unconverted hydroperoxide can be recycled into the reaction in step e). On the other hand, the pH is preferably selected at a sufficiently high level that carboxylic acid present in the reaction mixture is present in the form of a carboxylate salt in the aqueous phase to an extent of more than 80%, more preferably more than 90%, and only a small portion is present in the form of the free carboxylic acid in the organic phase. The selection of a sufficiently high pH prevents base from being consumed unnecessarily through the deprotonation of carboxylic acid in step d), and carboxylic acid being recycled into the reaction in the form of a carboxylate salt in step e) and being accumulated there.

If the reaction mixture obtained in step a) already has an aqueous phase having a pH in the inventive range and the organic hydroperoxide, as desired, is present predominantly in the organic phase, no addition of base or acid is required in step b). In general, an addition of acid will be required in step b) in order to achieve the desired pH and the desired distribution of organic hydroperoxide between aqueous phase and organic phase. In that case, preference is given to adding, in step b), a mineral acid, more preferably sulphuric acid or hydrochloric acid, in order to adjust the pH. When an acid anhydride is used as the acyl compound, however, an addition of a base may also be required in order to achieve the desired pH.

Subsequently, in step c), the biphasic mixture obtained in step b) is separated into an aqueous phase and an organic phase. As a result of the adjustment of the pH undertaken in step b), the aqueous phase removed in step c) comprises only small amounts of organic hydroperoxide and can therefore generally be sent without further pretreatment to a biological wastewater treatment. In contrast, the aqueous phase comprises the majority of the carboxylate salt formed in the reaction, which is removed from the acyl peroxide in step c).

Thereafter, in step d), the organic phase obtained in step c) is extracted with an aqueous solution of a base. The concentration of the base is preferably selected such that, in the extraction, the majority, more preferably more than 95%, of the organic hydroperoxide present in the organic phase is extracted into the aqueous phase in the form of the hydroperoxide salt and thus removed from the acyl peroxide, which remains in the organic phase. The amount of the aqueous solution of a base used for the extraction is preferably selected such that the amount of base present therein is not greater than the amount of base required for the reaction in step a).

Subsequently, in step e), the aqueous extract obtained in step d) is recycled into step a) with the organic hydroperoxide present therein in the form of the hydroperoxide salt. The recycling of the unconverted organic hydroperoxide allows virtually complete conversion of the hydroperoxide to the acyl peroxide to be achieved, even when organic hydroperoxide is used in excess.

The process according to the invention can be performed either continuously or batchwise in the individual steps, in which case it is also possible to combine continuous steps with batchwise steps.

In step a), the reaction of acyl compound and organic hydroperoxide is effected preferably in one or more mixed reactors in which good dispersion of the biphasic reaction mixture with formation of a high phase interface is ensured. Suitable mixed reactors are, for example, stirred tank reactors, loop reactors or tubular reactors with turbulent flow, the turbulence being generated by internals if appropriate. Preference is given to using cooled reactors in order to remove the heat of reaction released at approximately constant temperature. Particular preference is given to performing the reaction in step a) continuously in an arrangement of a plurality of mixed reactors connected in series.

In the case of preparation of acyl peroxides which are liquid under the reaction conditions used, the reaction in step a) is preferably performed without solvent.

Acyl compounds and/or organic hydroperoxides which are solid under the reaction conditions used are used in step a) preferably in the form of a solution in a solvent. Suitable solvents are all solvents known to those skilled in the art which react under the reaction conditions neither with the acyl compound nor with the organic hydroperoxide or the base. Preference is given to using solvents which, at the reaction temperature used, have a solubility in water of less than 1 g/l. Suitable solvents are, for example, toluene and isododecane.

In the preparation of acyl peroxides which are solid under the reaction conditions used, preference is given to adding a solvent for the acyl peroxide in an amount which ensures that, in step a), the organic phase obtained is a liquid solution of the acyl peroxide in the solvent. Preference is given to using solvents which, at the reaction temperature used, have a solubility in water of less than 1 g/l. Suitable solvents are, for example, toluene and isododecane.

The molar ratio of organic hydroperoxide to acyl compound in the reaction in step a) is preferably in the range of 1.01:1 to 2:1, more preferably 1.05:1 to 1.5:1. This molar ratio includes the amount of organic hydroperoxide which is recycled into the reaction through the recycling of the aqueous extract in step e). The excess of organic hydroperoxide relative to the acyl compound is preferably selected such that, in step a), a conversion of the acyl compound of more than 90%, more preferably more than 93%, is achieved.

The reaction of an acid chloride of the structure $R^1C(O)Cl$ or of a carboxylic anhydride of the structure $R^1C(O)OC(O)R^1$ with a hydroperoxide of the structure $R^2OOH$ affords, in step a), a percarboxylic ester of the structure $R^1C(O)OOR^2$. The acyl compound and the hydroperoxide are used preferably in a molar ratio of 1:1.01 to 1:2, more preferably 1:1.01 to 1:1.5. The molar ratio of acyl compound to base (preferably alkali metal hydroxide) is preferably in the range of 1:0.8 to 1:5, more preferably 1:1 to 1:3.5. If, in step a), in addition to the aqueous extract recycled with step e), an aqueous solution of a base is also added, this addition is preferably effected so as to give rise to a pH in the range of 8 to 14, preferably 11 to 14, in the aqueous phase of the reaction mixture. The reaction is effected preferably at a temperature in the range of −10 to 50° C., more preferably 10 to 40° C.

The reaction of a chloroformate of the structure $R^1OC(O)Cl$ with a hydroperoxide of the structure $R^2OOH$ in step a) affords a peroxomonocarbonate of the structure $R^1OC(O)OOR^2$. The chloroformate and the hydroperoxide are used preferably in a molar ratio of 1:1.01 to 1:2, more preferably 1:1.01 to 1:1.5. The molar ratio of chloroformate to base (preferably alkali metal hydroxide) is preferably in the range of 1:1 to 1:2, more preferably 1:1.2 to 1:1.5. If, in step a), in addition to the aqueous extract recycled with step e), an aqueous solution of a base is also added, this addition is preferably effected so as to give rise to a pH in the range of 8 to 14, preferably 10 to 14, in the aqueous phase of the reaction mixture. The reaction is effected preferably at a temperature in the range of −10 to 50° C., more preferably 0 to 40° C.

The acid chloride used is preferably a compound from the group of acetyl chloride, propionyl chloride, butyryl chloride, isobutyryl chloride, valeroyl chloride, 2-methylbutyryl chloride, pivaloyl chloride, 2-methylpentanoyl chloride, 2-ethylbutyryl chloride, 2-ethylhexanoyl chloride, nonanoyl chloride, 2,4,4-trimethylpentanoyl chloride, 3,5,5-trimethylhexanoyl chloride, decanoyl chloride, neodecanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride and naphthoyl chloride. The acid chloride used is more preferably pivaloyl chloride, 2-ethylhexanoyl chloride or benzoyl chloride.

The carboxylic anhydride used is preferably a compound from the group of acetic anhydride, succinic anhydride, maleic anhydride and phthalic anhydride.

The chloroformate used is preferably a compound from the group of methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, myristyl chloroformate, cetyl chloroformate, stearyl chloroformate, cyclohexyl chloroformate, 4-tert-butylcyclohexyl chloroformate, benzyl chloroformate and 2-phenoxyethyl chloroformate. The chloroformate used is more preferably 2-ethylhexyl chloroformate.

The organic hydroperoxide used is preferably a compound from the group of tert-butyl hydroperoxide, tert-amyl hydroperoxide, 1,1,3,3-tetramethylbutyl hydroperoxide, 2,5-dimethylhexane 2,5-dihydroperoxide, 2,5-dimethyl-3-hexyne 2,5-dihydroperoxide, p-menthane hydroperoxide, pinane hydroperoxide, tetralin hydroperoxide, cumene hydroperoxide, 4-tert-butylcumene hydroperoxide, 1,3-diisopropylbenzene dihydroperoxide and 1,4-diisopropylbenzene dihydroperoxide. The organic hydroperoxide used is more preferably tert-butyl hydroperoxide.

In step b), the pH is adjusted preferably in a continuous stirred tank, by keeping the pH of the aqueous phase at the desired value by pH-regulated addition of an acid or alkali.

The phase separation in step c) is effected in a known manner. Preference is given to performing steps b) and c) continuously in an apparatus known to those skilled in the art as a mixer-settler.

The extraction in step d) is performed preferably with an aqueous solution which contains more than 0.5 mol/l and more preferably more than 2 mol/l of base. The base used is preferably an alkali metal hydroxide and more preferably sodium hydroxide or potassium hydroxide. The use of a high concentration of base allows the amount of water which is recycled in step e) into the reaction of step a) to be kept low. This has the advantage that the apparatus used in steps a) to d) can have a smaller volume.

For the extraction in step d), it is possible to use all apparatus for liquid-liquid extraction known to those skilled in the art. Preference is given to performing the extraction continuously, more preferably in the form of a countercurrent extraction, in which the organic phase and the aqueous solution of the base are passed in countercurrent through the extraction apparatus. A countercurrent extraction is preferably designed such that a separation effect of 2 to 10 theoretical plates is achieved for the extraction of the organic hydroperoxide into the aqueous phase.

The extraction in step d) is performed preferably such that the contact time between the organic phase and the aqueous solution is less than 20 minutes, more preferably less than 2 minutes. The restriction of the contact time allows substantial prevention of hydrolysis of acyl peroxide by the aqueous solution of the base to give a carboxylate salt and hydroperoxide. The product loss through hydrolysis can also be kept low by performing the extraction preferably at a temperature in the range of 10 to 50° C., more preferably 15 to 30° C.

In a particularly preferred embodiment, the extraction in step d) is performed in a centrifugal extractor which is especially designed such that a multistage countercurrent extraction is effected with a contact time between organic phase and aqueous solution of less than 2 minutes. Suitable centrifugal extractors are known to those skilled in the art from the prior art, for example from Ullmann's Encyclopaedia of Chemical Technology, Vol. B3, pages 6-21 to 6-22.

The organic phase obtained from the extraction in step d) comprises the acyl peroxide and any solvent added in step a). This organic phase is preferably subjected to at least one wash in order to remove residues of basic aqueous phase dispersed in the organic phase and any residues of hydroperoxide. The wash is effected preferably with aqueous acid, to which may be added, in order to remove hydroperoxide, a suitable reducing agent preferably relatively insoluble in the organic phase. In the case of use of a centrifugal extractor, the wash can advantageously be effected in a section of the apparatus downstream from the extraction of step d), from which section the consumed wash solution is obtained separately from the aqueous extract from step d).

From the organic phase obtained in step d), optionally after a preceding wash, the water dissolved and/or dispersed in the organic phase is preferably also removed by drying. The drying can be brought about by water-absorbing absorbents, by drying in vacuo or by stripping with a gas stream. Preference is given to performing drying by stripping with a gas stream at a pressure in the range of 20 to 100 mbar and a temperature in the range of 10 to 50° C.

The process according to the invention allows for the preparation of acyl peroxides from an acyl compound and an organic hydroperoxide using an excess of hydroperoxide, without an elevated amount of hydroperoxide compared to the stoichiometric amount being consumed for the reaction. The use of an excess of hydroperoxide allows the reaction to be conducted more rapidly to high conversions of acyl compound, so that, in step a), a smaller reaction volume is required, which, besides savings in the apparatus, also leads to superior safety due to the smaller amount of acyl peroxide in the reactor. Since smaller amounts of dissolved hydroperoxide are discharged with the discharged aqueous phases in the process according to the invention, the process according to the invention also results in a lower wastewater pollution. The removal of unconverted hydroperoxide also affords, with the process according to the invention, a product with higher purity.

FIG. 1 shows a preferred embodiment of the process according to the invention using a centrifugal extractor.

In the preferred embodiment shown in FIG. 1, step a) is performed in a stirred tank with cooling jacket (1), to which are fed an acyl compound (2) and an organic hydroperoxide (3). Step b) is performed in a stirred vessel (4), to which is fed the biphasic reaction mixture from step a). In the stirred vessel (4), the desired pH is established in the aqueous phase by adding acid (5). The biphasic mixture obtained in step b) is fed to a vessel (6) in which step c) is effected, the separation into an aqueous phase an organic phase. The aqueous phase (7) obtained in step c) is discharged. The organic phase obtained in step c) is fed to a centrifugal extractor (8) in which it is extracted in a step d) with an aqueous solution of an alkali metal hydroxide (9). The aqueous extract obtained in step d) is, in a step e), recycled via a line (10) into the stirred tank (1) of step a). The amount of alkali metal hydroxide required in step a) in addition to the amount of alkali metal hydroxide present in solution (9) is fed to step a) as an aqueous solution of alkali metal hydroxide (11). The organic phase obtained in step e), which comprises the acyl peroxide and from which unconverted hydroperoxide has been removed can be subjected to further steps for washing and drying, which are not shown.

The examples which follow illustrate the process according to the invention, but without restricting it.

EXAMPLES

Experimental Procedure

The reaction is effected in a reactor arrangement of a loop reactor of volume 2.2 l, in which the reaction mixture is conducted through a heat exchanger with a pump at a flow rate of 1 m³/h, and a downstream stirred cell reactor with 6 chambers, each of volume 1.7 l, arranged one on top of another, and a common cooling jacket, adjacent chambers each being connected to one another via passages. A stirrer is mounted in each chamber, all stirrers being driven by means of a common shaft. The stirred cell reactor thus corresponds to 6 continuous stirred tank reactors connected in series. The feedstocks are fed into the loop reactor into the connecting line immediately upstream of the circulation pump. The reaction mixture withdrawn from the loop reactor is fed to the lowermost chamber of the stirred cell reactor; the converted reaction mixture is withdrawn by overflow from the uppermost chamber of the stirred cell reactor. The reaction mixture is then fed to a continuous, cooled stirred tank in which partial neutralization to a pH in the range of 10 to 12 is effected by adding aqueous hydrochloric acid, and solvent is optionally added. The partially neutralized reaction mixture is then separated in a settler into an aqueous phase and an organic phase. The organic phase is subsequently extracted in a centrifugal extractor in countercurrent with an aqueous solution of potassium hydroxide, and the resulting aqueous extract is recycled into the loop reactor. The organic phase is washed after the extraction and dried by stripping in a packed column in vacuo.

Example 1

Preparation of tert-butyl peroxypivalate

Before the start of the reaction, the loop reactor is filled with a solution of 26.0% by weight of tert-butyl hydroperoxide and 16.2% by weight of potassium hydroxide in water. Initially 26.0 kg/h of a solution of 70% by weight of tert-butyl hydroperoxide in water, 25.0 kg/h of a solution of 45% by weight of potassium hydroxide in water, 26.4 kg/h of water and 18.0 kg/h of pivaloyl chloride are then fed to the loop reactor. Cooling with cooling water keeps the internal temperature at 15° C. in the loop reactor and at 10° C. in the stirred cell reactor. The partial neutralization is effected with 6.0 kg/h of 31% by weight hydrochloric acid with addition of 8.2 kg/h of isododecane at a temperature of 8° C. The organic phase is extracted with 33.2 kg/h of a 20% by weight aqueous solution of potassium hydroxide. This affords 37.4 kg/h of aqueous extract comprising 11.6% by weight of tert-butyl hydroperoxide and 17.6% by weight of potassium hydroxide, which are feeded into the loop reactor. From the time at which aqueous extract is recycled into the loop reactor, the metered addition of the feedstocks is changed to 19.8 kg/h of a solution of 70% by weight of tert-butyl hydroperoxide in water, 10.2 kg/h of a solution of 45% by weight of potassium hydroxide in water and 9.8 kg/h of water. After the extraction, the organic phase is washed with 36.0 kg/h of a solution of 1% by weight of sodium sulphite and 0.2% by weight of sulphuric acid, and dried by stripping at 20° C. and 45 mbar. 32.4 kg/h of a 75.3% by weight solution of tert-butyl peroxypivalate in isododecane are obtained (93.7% yield based on pivaloyl chloride).

In operation with recycling of the extracted tert-butyl hydroperoxide, the molar ratio of the tert-butyl hydroperoxide to pivaloyl chloride feedstocks is 1.03:1.

Example 2

Preparation of tert-butyl peroxy-2-ethylhexanoate

Before the start of the reaction, the loop reactor is filled with a solution of 25.8% by weight of tert-butyl hydroperoxide and 16.4% by weight of potassium hydroxide. Initially 24.6 kg/h of a solution of 70% by weight of tert-butyl hydroperoxide in water, 24.0 kg/h of a solution of 45% by weight of potassium hydroxide in water, 17.4 kg/h of water and 24.0 kg/h of 2-ethylhexanoyl chloride are then fed to the loop reactor. Cooling with cooling water keeps the internal temperature at 35° C. in the loop reactor and at 27° C. in the stirred cell reactor. The partial neutralization is effected with 5.4 kg/h of 31% by weight hydrochloric acid with addition of 6.0 kg/h of water at a temperature of 18° C. The organic phase is extracted with 26.0 kg/h of a 15% by weight aqueous solution of potassium hydroxide. This affords 29.2 kg/h of aqueous extract comprising 10.8% by weight of tert-butyl hydroperoxide and 13.4% by weight of potassium hydroxide, which are feeded into the loop reactor. From the time at which the aqueous extract is recycled into the loop reactor, the metered addition of the feedstocks is changed to 20.0 kg/h of a solution of 70% by weight of tert-butyl hydroperoxide in water, 15.4 kg/h of a solution of 45% by weight of potassium hydroxide in water and 1.4 kg/h of water. After the extraction, the organic phase is washed with 36.0 kg/h of a solution of 1% by weight of sodium sulphite and 0.2% by weight of sulphuric acid, and dried by stripping at 33° C. and 40 mbar. 31.6 kg/h of tert-butyl peroxy-2-ethylhexanoate are obtained with a purity of 99.3% (98.5% yield based on 2-ethylhexanoyl chloride).

In operation with recycling of the extracted tert-butyl hydroperoxide, the molar ratio of the tert-butyl hydroperoxide to 2-ethylhexanoyl chloride feedstocks is 1.05:1.

Example 3

Preparation of tert-amyl peroxypivalate

Before the start of the reaction, the loop reactor is filled with a solution of 23.1% by weight of tert-amyl hydroperoxide, 9.9% by weight of potassium hydroxide and 8.3% by weight of sodium hydroxide in water. Initially 20.0 kg/h of a solution of 88% by weight of tert-amyl hydroperoxide in water, 15.8 kg/h of a solution of 45% by weight of potassium hydroxide in water, 11.8 kg/h of a solution of 50% by weight of sodium hydroxide in water, 24.2 kg/h of water and 18.0 kg/h of pivaloyl chloride are then fed to the loop reactor. Cooling with cooling water keeps the internal temperature at 18° C. in the loop reactor and at 10° C. in the stirred cell reactor. The partial neutralization is effected with 11.4 kg/h of 31% by weight hydrochloric acid with addition of 7.4 kg/h of isododecane at a temperature of 10° C. The organic phase is extracted with 27.8 kg/h of a 16% by weight aqueous solution of potassium hydroxide. This affords 29.4 kg/h of aqueous extract comprising 5.8% by weight of tert-amyl hydroperoxide and 15.1% by weight of potassium hydroxide, which are feeded into the loop reactor. From the time at which aqueous extract is recycled into the loop reactor, the metered addition of the feedstocks is changed to 18.2 kg/h of a solution of 88% by weight of tert-amyl hydroperoxide in water, 5.8 kg/h of a solution of 45% by weight of potassium hydroxide in water and 6.6 kg/h of water. After the extraction, the organic phase is washed with 36 kg/h of a solution of 5% by weight of sodium sulphite and 0.2% by weight of sulphuric acid, and dried by stripping at 20° C. and 45 mbar. 34.4 kg/h of a 76.6% by weight solution of tert-amyl peroxypivalate in isododecane are obtained (93.9% yield based on pivaloyl chloride).

In operation with recycling of the extracted tert-amyl hydroperoxide, the molar ratio of the tert-amyl hydroperoxide to pivaloyl chloride reactants is 1.03:1.

Example 4

Preparation of tert-butyl peroxy-3,5,5-trimethylhexanoate

Before the start of the reaction, the loop reactor is filled with a solution of 25.7% by weight of tert-butyl hydroperoxide and 15.0% by weight of potassium hydroxide in water. Initially 20.2 kg/h of a solution of 70% by weight of tert-butyl hydroperoxide in water, 18.2 kg/h of a solution of 45% by weight of potassium hydroxide in water, 16.2 kg/h of water and 19.2 kg/h of 3,5,5-trimethylhexanoyl chloride are then fed to the loop reactor. Cooling with cooling water keeps the internal temperature at 25° C. in the loop reactor and in the stirred cell reactor. The partial neutralization is effected with 27.6 kg/h of 4% by weight hydrochloric acid at a temperature of 15° C. The organic phase is extracted with 23.6 kg/h of a 20% by weight aqueous solution of potassium hydroxide. This affords 26.2 kg/h of aqueous extract comprising 9.6% by weight of tert-butyl hydroperoxide and 18.0% by weight of potassium hydroxide, which are feeded into the loop reactor. From the time at which aqueous extract is recycled into the loop reactor, the metered addition of the feedstocks is changed to 16.6 kg/h of a solution of 70% by weight of tert-butyl hydroperoxide in water, 7.8 kg/h of a solution of 45% by weight of potassium hydroxide in water and 4.8 kg/h of water. After the extraction, the organic phase is washed with 33.8 kg/h of a solution of 3% by weight of sodium sulphite and 1% by weight of sulphuric acid, and dried by stripping at 34° C. and 47 mbar. 24.6 kg/h of tert-butyl peroxy-3,5,5-trimethylhexanoate with a purity of 99.9% are obtained (98.2% yield based on 3,5,5-trimethylhexanoyl chloride).

In operation with recycling of the extracted tert-butyl hydroperoxide, the molar ratio of the tert-butyl hydroperoxide to 3,5,5-trimethylhexanoyl chloride feedstocks is 1.19:1.

Example 5

Preparation of tert-butyl peroxyisobutyrate

Before the start of the reaction, the loop reactor is filled with a solution of 24.4% by weight of tert-butyl hydroperoxide and 12.7% by weight of potassium hydroxide in water. Initially 33.6 kg/h of a solution of 70% by weight of tert-butyl hydroperoxide in water, 27.0 kg/h of a solution of 45% by weight of potassium hydroxide in water, 35.0 kg/h of water and 18.4 kg/h of isobutyroyl chloride are then fed to the loop reactor. Cooling with cooling water keeps the internal temperature at 11° C. in the loop reactor and at 12° C. in the stirred cell reactor. The partial neutralization is effected with 3.6 kg/h of 31% by weight hydrochloric acid with addition of 8.0 kg/h of isododecane at a temperature of 8° C. The organic phase is extracted with 33.0 kg/h of a 15% by weight aqueous solution of potassium hydroxide. This affords 39.8 kg/h of aqueous extract comprising 17.1% by weight of tert-butyl hydroperoxide and 12.2% by weight of potassium hydroxide, which are feeded into the loop reactor. From the time at which aqueous extract is recycled into the loop reactor, the metered addition of the feedstocks is changed to 23.8 kg/h of a solution of 70% by weight of tert-butyl hydroperoxide in water, 16.0 kg/h of a solution of 45% by weight of potassium hydroxide in water and 15.8 kg/h of water. After the extraction, the organic phase is washed with 36 kg/h of a solution of 3% by weight of sodium sulphite and 1% by weight of sulphuric acid, and dried by stripping at 18° C. and 58 mbar. 33.4 kg/h of a 76.5% by weight solution of tert-butyl peroxyisobutyrate in isododecane are obtained (92.8% yield based on isobutyroyl chloride).

In operation with recycling of the extracted tert-butyl hydroperoxide, the molar ratio of the tert-butyl hydroperoxide to isobutyroyl chloride feedstocks is 1.07:1.

Example 6

Preparation of tert-butyl peroxybenzoate

Before the start of the reaction, the loop reactor is filled with a solution of 19.6% by weight of tert-butyl hydroperoxide and 9.0% by weight of sodium hydroxide. Initially 18.4 kg/h of a solution of 70% by weight of tert-butyl hydroperoxide in water, 11.8 kg/h of a solution of 50% by weight of sodium hydroxide in water, 35.2 kg/h of water and 18.0 kg/h of benzoyl chloride are then fed to the loop reactor. Cooling with cooling water keeps the internal temperature at 12° C. in the loop reactor and at 11° C. in the stirred cell reactor. The partial neutralization is effected with 2.2 kg/h of 31% by weight hydrochloric acid with addition of 6.0 kg/h of water at a temperature of 16° C. The organic phase is extracted with 17.2 kg/h of a 15% by weight aqueous solution of sodium hydroxide. This affords 18.4 kg/h of aqueous extract comprising 6.3% by weight of tert-butyl hydroperoxide and 14.1% by weight of sodium hydroxide, which are feeded into the loop reactor. From the time at which aqueous extract is recycled into the loop reactor, the metered addition of the feedstocks is changed to 16.8 kg/h of a solution of 70% by weight of tert-butyl hydroperoxide in water, 6.6 kg/h of a solution of 50% by weight of sodium hydroxide in water and 23.0 kg/h of water. After the extraction, the organic phase is washed with 36 kg/h of a solution of 1% by weight of sodium sulphite and 0.4% by weight of sulphuric acid, and dried by stripping at 35° C. and 43 mbar. 23.8 kg/h of tert-butyl peroxybenzoate with a purity of 99.7% are obtained (95.3% yield based on benzoyl chloride).

In operation with recycling of the extracted tert-butyl hydroperoxide, the molar ratio of the tert-butyl hydroperoxide to benzoyl chloride feedstocks is 1.02:1.

The invention claimed is:

1. A process for preparing an acyl peroxide, comprising:
   a) reacting an acyl compound, an organic hydroperoxide and an aqueous solution of a base to obtain a biphasic reaction mixture, said biphasic reaction mixture containing an aqueous phase and an organic phase,
   b) adjusting the pH of the aqueous phase of the biphasic reaction mixture obtained in step a) to 6 to 13,
   c) separating the biphasic mixture obtained in step b) into an aqueous phase and an organic phase,
   d) extracting the organic phase obtained in step c) with an aqueous solution of a base to obtain an aqueous extract and
   e) recycling the aqueous extract obtained in step d) into step a),
   wherein said acyl compound is selected from the group consisting of an acid chloride, a carboxylic anhydride and a chloroformate.

2. The process of claim 1, comprising adjusting said pH to 11 to 12.5.

3. The process of claim 1, wherein said organic hydroperoxide and said acyl compound are present at a ratio in a range from 1.01 to 2.

4. The process of claim 1, wherein said organic hydroperoxide and said acyl compound are present at a ratio in a range from 1.05 to 1.5.

5. The process of claim 1, wherein the aqueous solution of a base in step d) is present at a concentration of more than 0.5 mol/l.

6. The process of claim 1, wherein the aqueous solution of a base in step d) is present at a concentration of more than 2 mol/l.

7. The process of claim 1, wherein the extraction in step d) comprises a countercurrent extraction.

8. The process of claim 1, wherein said organic phase and said aqueous solution in step d) are in contact for less than 20 minutes.

9. The process of claim 1, wherein said organic phase and said aqueous solution in step d) are in contact for less than 2 minutes.

10. The process of claim 1, comprising extracting said organic phase in a centrifugal extractor.

11. The process of claim 1, wherein the acyl compound is an acid chloride selected from the group consisting of an acetyl chloride, a propionyl chloride, a butyryl chloride, an isobutyryl chloride, a valeroyl chloride, a 2-methylbutyryl chloride, a pivaloyl chloride, a 2-methylpentanoyl chloride, a 2-ethylbutyryl chloride, a 2-ethylhexanoyl chloride, a nonanoyl chloride, a 2,4,4-trimethylpentanoyl chloride, a 3,5,5-trimethylhexanoyl chloride, a decanoyl chloride, a neodecanoyl chloride, a lauroyl chloride, a benzoyl chloride, a 2-methylbenzoyl chloride, a 4-methylbenzoyl chloride, a 4-chlorobenzoyl chloride, a 2,4-dichlorobenzoyl chloride and a naphthoyl chloride.

12. The process of claim 1, wherein the acyl compound is a chloroformate selected from the group consisting of a methyl chloroformate, an ethyl chloroformate, a n-propyl chloroformate, an isopropyl chloroformate, a n-butyl chloroformate, a sec-butyl chloroformate, a 2-ethylhexyl chloroformate, an isotridecyl chloroformate, a myristyl chloroformate, a cetyl chloroformate, a stearyl chloroformate, a cyclohexyl chloroformate, a 4-tert-butylcyclohexyl chloroformate, a benzyl chloroformate and a 2-phenoxyethyl chloroformate.

13. The process of claim 1, wherein the organic peroxide is selected from the group consisting of a tert-butyl hydroperoxide, a tert-amyl hydroperoxide, a 1,1,3,3-tetramethylbutyl hydroperoxide, a 2,5-dimethylhexane 2-5-dihydroperoxide, a 2-5-dimethyl-3-hexyne 2,5-dihydroperoxide, a p-menthane hydroperoxide, a pinane hydroperoxide, a tetralin hydroperoxide, a cumene hydroperoxide, a 4-tert-butylcumene hydroperoxide, a 1,3-diisopropylbenzene dihydroperoxide and a 1,4-diisopropylbenzene dihydroperoxide.

\* \* \* \* \*